US005401920A

United States Patent [19]

Oliveira

[11] Patent Number: 5,401,920

[45] Date of Patent: Mar. 28, 1995

[54] CERUMEN FILTER FOR HEARING AIDS

[76] Inventor: Robert J. Oliveira, 200 Crestview Dr., Maplewood, Minn. 55119

[21] Appl. No.: 53,818

[22] Filed: Apr. 29, 1993

Related U.S. Application Data

[63] Continuation of Ser. No. 803,576, Dec. 9, 1991, abandoned.

[51] Int. Cl.[6] .......... A61B 7/02

[52] U.S. Cl. .......... 181/135

[58] Field of Search .......... 181/130, 131, 135; 381/68.6, 68, 69; 128/152, 864, 867, 414

[56] References Cited

U.S. PATENT DOCUMENTS

| | | | |
|---|---|---|---|
| 3,414,685 | 12/1968 | Geib et al. | 181/135 |
| 4,553,627 | 11/1985 | Gastmeier et al. | 181/135 |
| 4,679,650 | 7/1987 | Moser et al. | 181/130 |
| 4,724,922 | 2/1988 | Kalayjian | 181/135 |
| 4,751,731 | 6/1988 | O'Connor | 379/439 |
| 4,800,982 | 1/1989 | Carlson | 181/130 |
| 4,870,689 | 9/1989 | Weiss | 381/68.6 |
| 4,953,215 | 1/1990 | Weiss et al. | 381/68 |
| 4,972,488 | 11/1990 | Weiss et al. | 381/68.6 |
| 4,984,277 | 1/1991 | Bisgaard et al. | 381/69.2 |
| 5,002,151 | 3/1991 | Oliveira et al. | 181/130 |

FOREIGN PATENT DOCUMENTS

| | | |
|---|---|---|
| 0310866 | 12/1989 | European Pat. Off. . |
| 2818273 | 11/1979 | Germany . |
| 2155276 | 9/1985 | United Kingdom . |

*Primary Examiner*—Michael L. Gellner
*Assistant Examiner*—Khanh Dang
*Attorney, Agent, or Firm*—Richard E. Brink

[57] ABSTRACT

A readily installed and replaced disposable wax guard that is affixed over the sound outlet port of an "in the ear" hearing aid and adhered to the adjacent sides of the aid. The portion that overlies the sound outlet port is porous to sound and receptive to cerumen.

20 Claims, 3 Drawing Sheets

CERUMEN FILTER FOR HEARING AIDS

This is a continuation of application Ser. No. 07/803,576, filed Dec. 9, 1991, now abandoned.

BACKGROUND OF THE INVENTION

This invention relates to preventing cerumen, or ear wax, from interfering with the operation of sound transmission devices, especially "in the ear" hearing aids, and is particularly concerned with a novel filter for achieving that result.

The human outer ear comprises the visible external ear, or pinna, and a dynamic S-shaped canal that has a generally oval cross section and is about an inch (2.5 cm) long. Cerumen is secreted by the walls of the canal in the outer half inch (1.2 cm) or so and gradually moved outward; some believe that this outward movement is brought about by cilia in the walls, but more likely it is caused by the natural action of the ear canal. When a hearing aid is inserted into the outer ¼ inch (about 0.6 cm) of the canal, it becomes susceptible to cerumen, which mixes with sloughed off skin and often fouls the hearing aid's sound delivery tube, thereby reducing its efficiency.

When the sound delivery tube of a hearing aid clogs with cerumen and reduces the effectiveness of sound transmission, the wearer of a hearing aid typically turns up the volume control. This in turn results in two undesirable conditions. Not only does the hearing aid battery wear out more quickly with certain types of circuit, but the likelihood of embarrassing and frequently painful feedback howl also increases. Most importantly, cerumen in the sound tube of the hearing aid is the basis for large numbers of costly hearing aid repairs.

There have been numerous attempts to modify hearing aids to avoid the problems discussed in the preceding paragraphs. Thus, for example, U.S. Pat. Nos. 4,870,689 and 4,972,488 disclose a tubular passage having a series of baffles that define a "tortuous path" that the wax must travel before reaching the sound tube. U.S. Pat. No. 4,800,982 describes a hearing aid through which solvent may be pumped to remove wax buildup. U.S. Pat. No. 4,953,215 describes a hearing aid in which a domed membrane having a small central opening is provided, wax being said to accumulate in a ring around the base of the membrane.

Still others have attempted to devise some type of filter to prevent ear wax from reaching the sound delivery tube. For example, U.S. Pat. Nos. 3,414,685 and 4,984,277 discuss various prior art wax filters, noting the apparent difficulty in replacing them after they are soiled. In each case, the patentees' approach to the problem is to provide a one-piece plastic part that has numerous openings around the periphery and snaps around the sound delivery tube opening. A somewhat similar device is shown in U.S. Pat. No. 4,553,627, where a snap-on wax guard has a cross passage through its head that intersects an axial passage in its stem; ear wax is removed by pushing a tool through the cross passage. Still others have mechanically mounted screens or other filters beyond the sound delivery tube opening, but removal and replacement has been difficult, especially since persons wearing hearing aids are often advanced in years and unable either to see clearly enough or to perform fine physical actions well enough to replace the filters.

BRIEF SUMMARY

The present invention provides a novel disposable wax guard for sound transmission devices that are inserted into the ear canal, especially "in the ear" hearing aids. It is simple to install, easy to remove, and convenient to replace, even for older persons. The guard is inexpensive and requires no tools for installation or removal. In many instances, the wax guard of the invention not only assists in retaining the sound transmission device in place in the ear canal but also improves the seal between the hearing aid and the dynamic ear canal. Although the use of the invention with such sound transmission devices as stethoscopes, miniaturized portable telephones, etc., is envisioned, for convenience, the major part of the description that follows will be addressed to "in the ear" hearing aids.

An "in the ear" hearing aid comprises a housing containing a microphone, a battery, an amplifier, and a speaker, the housing fitting within a user's ear canal. A sound-transmitting tube extends from the speaker to an outlet port at the portion of the housing closest to the ear drum. The present invention provides a readily installed and replaced disposable wax guard for mounting over the outlet port of the hearing aid to prevent cerumen from fouling it. This wax guard comprises a thin, strong carrier membrane adapted to be temporarily adhered over the portion of the hearing aid nearest to the ear drum, fixed in position over the outlet port, the portion of the guard overlying the outlet port being porous to sound and receptive to cerumen and the accompanying dermal detritus from the lining of the ear canal before it can foul the sound outlet port of the hearing aid. In another aspect, the invention provides a method of modifying a conventional "in the ear" hearing aid to render it resistant to cerumen. In still another aspect, the invention provides a method of forming an improved seal between the hearing aid and the dynamic ear canal. In a further aspect, the invention provides improved retention of small earpieces in the dynamic ear canal.

BRIEF DESCRIPTION OF THE DRAWING

Understanding of the invention will be enhanced by referring to the accompanying drawing, in which like numbers refer to like parts in the several views, and in which.

DETAILED DESCRIPTION

Figure 1:
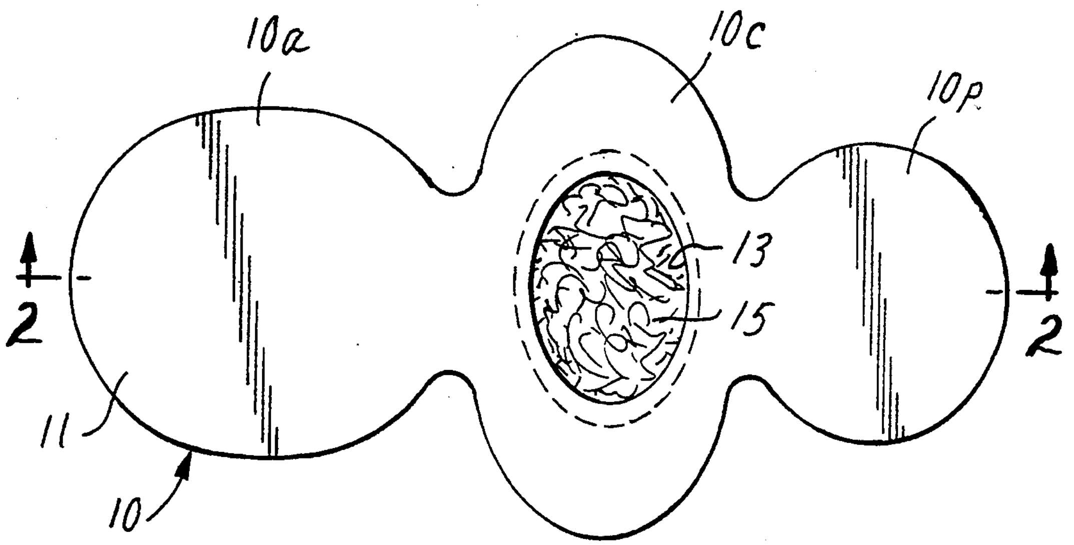
FIG. 1 is a greatly enlarged plan view of one embodiment of the wax guard of the invention.
Figure 2:
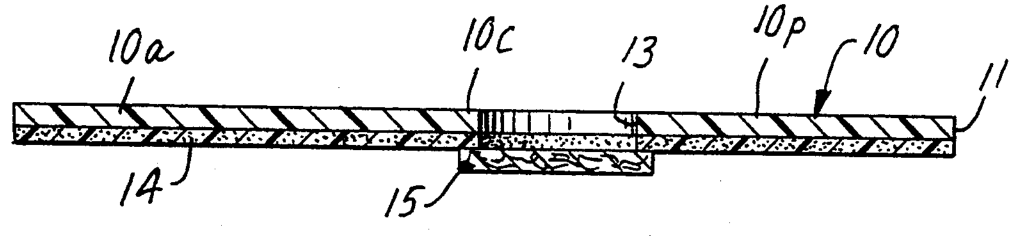
FIG. 2 is a cross-section of the wax guard of FIG. 1, taken along section line 2—2, looking in the direction of the arrows.

Turning first to FIGS. 1 and 2, wax guard 10 comprises thin, strong, flexible carrier membrane 11 having attaching lobes 10a, 10p, and central lobe 10c, hole 13 being located approximately in the center of lobe 10c. One side of carrier membrane 11 is provided with a layer of normally tacky and pressure-sensitive adhesive 14, which serves to affix wax guard 10 to a hearing aid, with hole 13 positioned over the sound outlet port of the hearing aid. A nonwoven mat 15 of fine fibers is held in place by adhesive 14 in the area circumjacent to hole 13. If desired, hole 13 may be covered with a mesh fabric to help retain mat 15 in place.

Carrier membrane 11 is conveniently made from a white rayon acetate taffeta woven backing, combined with a layer of pressure-sensitive adhesive 14, the mild rugosity of the backing imparting a desirable frictional property when wax guards of the invention are used as subsequently described. One adhesive-coated product suitable for use in practice of the invention is available from Minnesota Mining and Manufacturing Company (3M) under the catalog designation "1538-L Woven Medical Tape on Liner." The adhesive on this product is a hypoallergenic acrylate, making it especially suitable for practicing the present invention.

Nonwoven mat 15 is desirably formed from a melt-blown mat of extremely fine oleophilic polypropylene fibers. Alternatively, the mat could be an appropriately sized disc formed from a web of oleophilic open cell foam.

Figure 3:
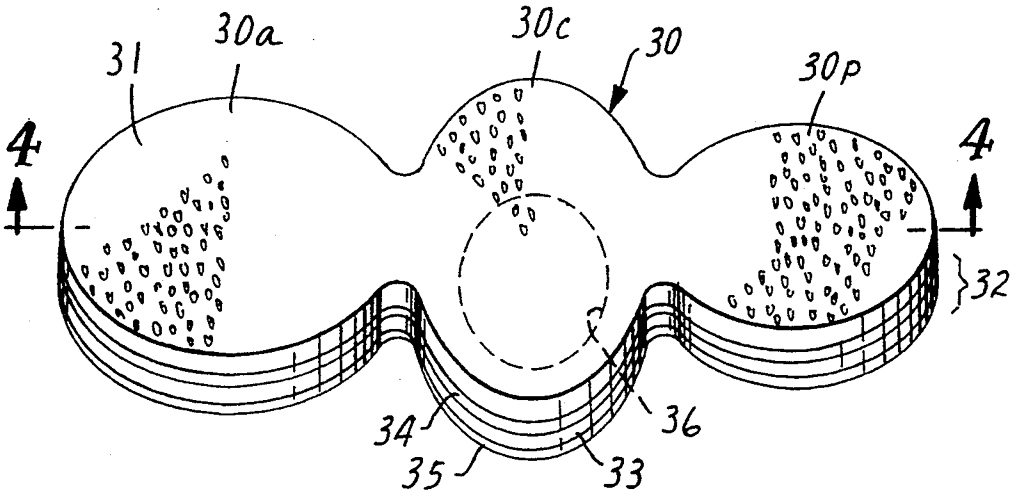
FIG. 3 is a view in perspective of a currently preferred embodiment of the invention.
Figure 4:
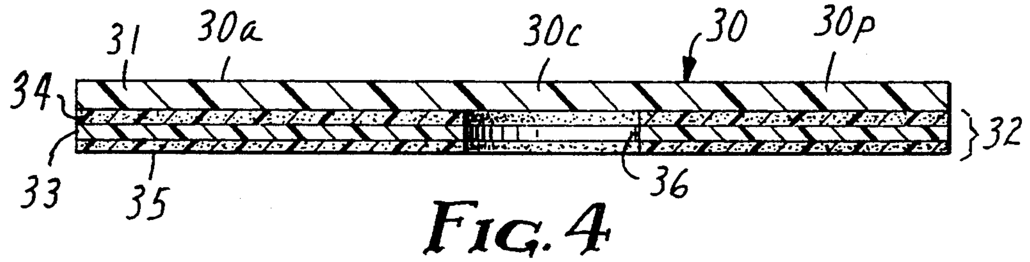
FIG. 4 is a cross-sectional view of the wax guard of FIG. 3, taken along section lines 4—4, looking in the direction of the arrows.
Figure 5:
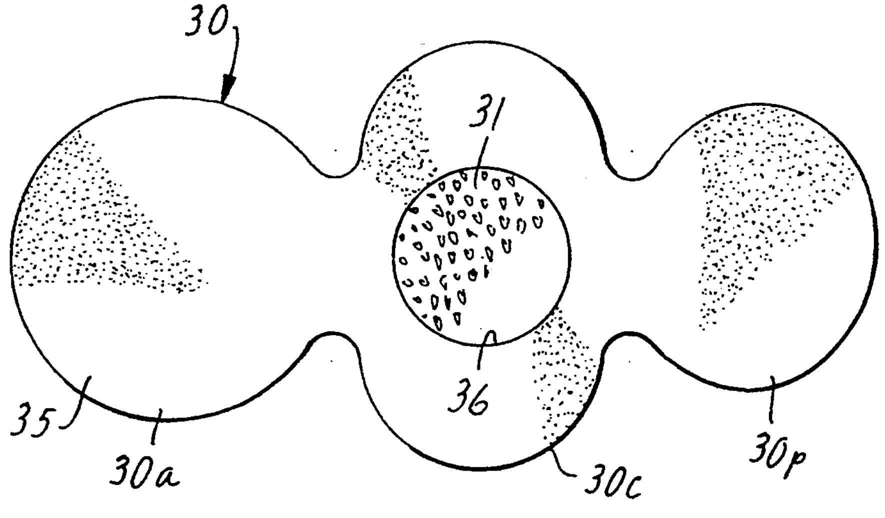
FIG. 5 is a plan view of the lower adhesive-coated surface of the wax guard of FIG. 3.

Turning next to FIGS. 3–5, wax guard 30 comprises a thin, compressible, resilient, sound-transmitting, soft membrane layer 31 of reticulated open cell microporous foam. Wax guard 30 in turn comprises anterior and posterior attaching lobes 30a, 30p, and central lobe 30c. Laminated to the lower surface of foam membrane layer 31 is double-coated tape 32, comprising thin (about 0.0015-inch, or 6-micrometer) polyethylene film 33 and pressure-sensitive adhesive layers 34, 35. Central portion 36 of lobe 30c is free from tape 32. Thus, whereas tape 32 seals foam membrane 31 and destroys its sound-transmitting ability, central portion 36 remains open and continues to retain that ability. This embodiment of the invention is thus both simple and economical to make.

Figure 6:
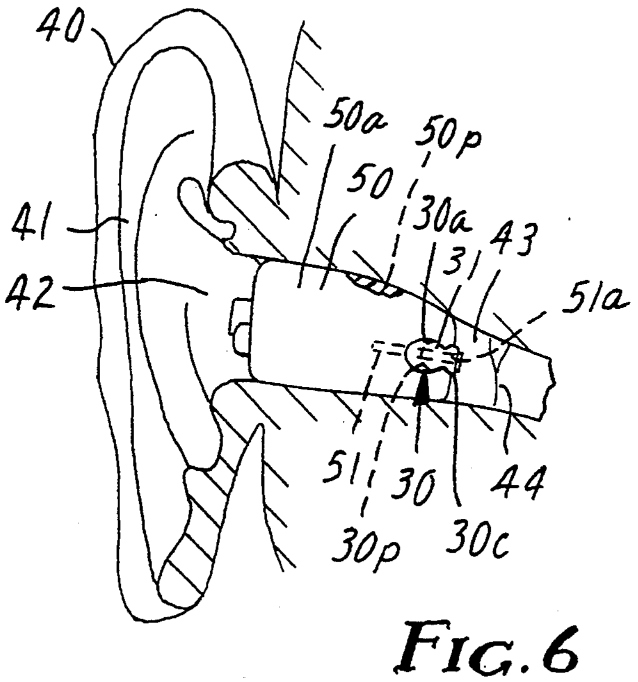
FIG. 6 is an enlarged and simplified drawing of a human ear, showing an "in the ear" hearing aid, partially broken away to assist in understanding, mounted in the ear canal, with a wax guard of the invention in place.

Attention is now directed to FIG. 6, showing wax guard 30 of FIG. 3 mounted on hearing aid 50. As is shown in FIG. 6, human outer ear 40 comprises pinna 41, concha 42, ear canal 43, and ear drum 44. Positioned within the outer portion of canal 22 is hearing aid 50, which includes the conventional battery, microphone, amplifier, and speaker (none of which are shown), with open-ended sound-transmitting tube 51 extending from the speaker to the inner end of hearing aid 50 and terminating in outlet port 56. Hearing aid 50 has anterior side 50a and posterior side 50p, the latter confronting the posterior side of canal 22, which is exposed in the drawing. Anterior side 50a confronts the anterior side of canal 22, which is not shown in the drawing. Wax guard 30 is positioned so that area 36 (which, it will be recalled, is free from pressure-sensitive adhesive tape) is mounted over the outlet port of sound transmitting tube 51, with adhesive-coated circumferential area 30c and lobes 30a and 30p adhered, respectively, to the inner end and anterior and posterior sides of hearing aid 50 to hold wax guard 30 in place. As previously pointed out, the outer portion of canal 43 is oval rather than circular in cross section, with the longer axis extending in a generally vertical plane. This ovality is reflected in the shape of central portion 31c of wax guard 30, and lobes 30a and 30p are accordingly intended to be mounted along the anterior and posterior sides of hearing aid 50. This positioning also provides a somewhat snugger fit between hearing aid 50 and the wall of canal 43 and helps hold hearing aid 50 in place. This is especially important when chewing or talking causes the anterior wall of canal 43 to move in and out, which in turn causes the anterior-posterior dimension of the oval canal wall to contract and expand.

It will be noted that posterior attaching lobe 30p is smaller than anterior attaching lobe 30a, enabling it to conform easily to the concave posterior surface of any hearing aid. This is especially important for those hearing aids that are seated in concha 42, which do not extend to a great depth in canal 43 and have other plastic surfaces that can interfere with easy access to the concave posterior side of the canal-occupying part of the hearing aid.

Because foam membrane 31 is not only compressible but also resilient, sealing of hearing aid 50 against the wall of canal 43 can be maintained, even as the dimensions of canal 43 change during mastication or conversation. This improved sealing helps correct the extremely annoying feedback problem frequently encountered by hearing aid wearers while dining with friends. Indeed, it is contemplated by the inventor that different thicknesses or surface areas of foam layer 31 can be employed to achieve the desired result. Inasmuch as improper fit is one of the most frequent complaints made by persons who have just purchased hearing aids, it is believed that use of the wax guard of this embodiment of the invention may reduce such complaints. With respect to the improved sealing provided by the foam, attention is directed to the prior art product ER-13R "E-A-R RING", a ring formed from foam and intended to be slipped over the distal portion of a hearing aid to "seal leaky shells" and reduce feedback. Prior art devices of this type, which are available from Etymotic Research, Elk Grove Village, Ill., USA, are not provided with pressure-sensitive adhesive (presumably because they would then be hard to install on a hearing aid), although the use of a drop of a permanent adhesive (e.g., tetrahydrofuran, which is presumably a solvent for the hearing aid 50) is suggested. In the absence of adhesive, these rings have been known to remain in the ear canal after removal of the hearing aid, and if a strong adhesive is used, it will be hard to remove the ring from the hearing aid.

A currently preferred material for use as foam layer 31 is a polyester urethane foam about 0.05 inch (1.3 mm) thick, having about 100 pores per lineal inch (40 pores per lineal centimeter) and a void volume of about 97%. As mentioned previously, however, somewhat greater thicknesses may be appropriate for some individuals. This foam is also oleophilic, which is considered advantageous for use as a wax guard. Foams meeting these criteria are obtainable from Foamex under the trade designation "SIF Filter Foam."

It is believed that a degree of stretchability of the foam product just described is desirable in attaining wrinkle-free conformance to hearing aids; thus, it may be feasible to provide one surface of reticulated foam directly with an adhesive. Greater strength can be imparted, however, by laminating the foam to a fine open mesh woven or nonwoven fabric (either of which might cover hole 36, 86, 96 without interfering with sound transmission) or, as in the product just described, to a double-coated tape.

Figure 7:
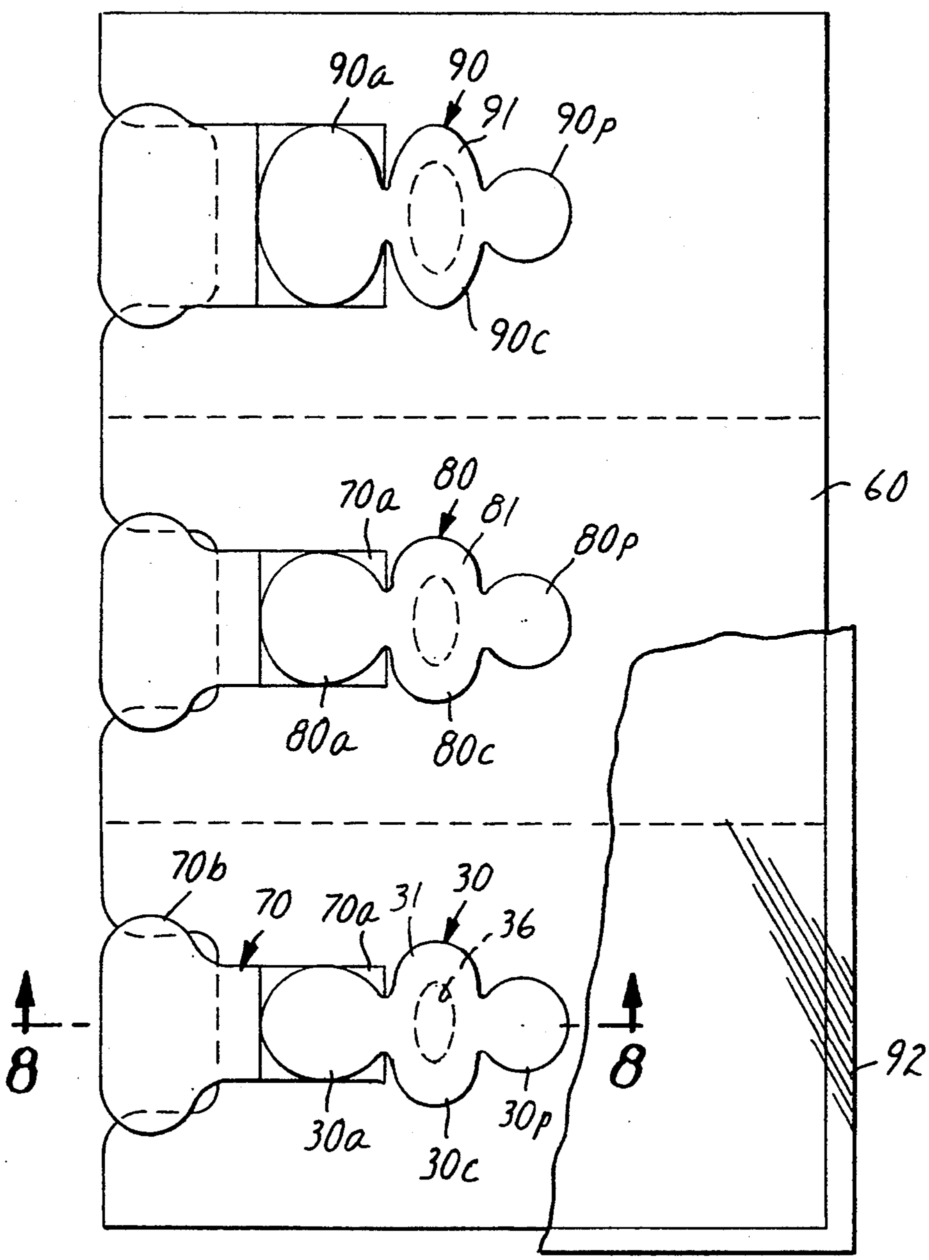
FIG. 7 is a greatly enlarged plan view showing three wax guards of the type shown in FIG. 3 (the exact dimensions differing among the three), positioned on a release liner, with a folded release liner protecting each of the lobes of each wax guard.
Figure 8:
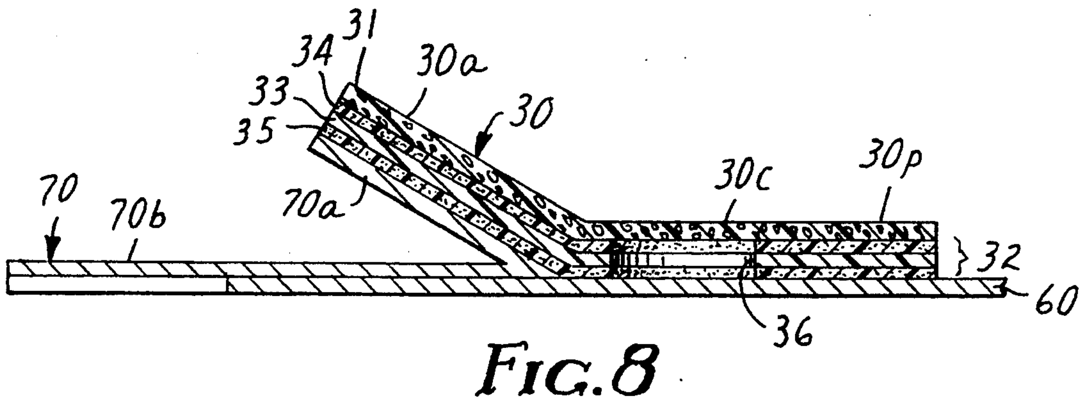
FIG. 8 is a cross-sectional view of the assembly shown in FIG. 7, taken along section line 8—8, looking in the direction of the arrows.

Attention is now directed to FIG. 7, which depicts the manner in which wax guards of the invention can be mounted for distribution to hearing aid dispensers or wearers of "in the ear" hearing aids. Three wax guards 30, 80, 90 are shown removably mounted on a conventional sheet of release liner 60, the adhesive-coated surface of posterior attaching lobes **30*p*, 80*p*, 90*p*, and central lobe 30*c*, 80*c*, 90*c* being in contact with the release surface of liner 60. Anterior attaching lobes 30*a*, 80*a*, 90*a* are lifted above the surface of release liner 60, with folded release liner 70 contacting the adhesive-coated surface of lobes 30*a*, 80*a*, 90*a*. Liner 70 has two wings, 70*a* and 70*b*, the adhesive-coated surface of lobes 30*a*, 80*a*, 90*a* being in contact with wing 70*a*. When wax guard 30, 80, or 90 is to be mounted on hearing aid 50, the distal portion of wing 70*b* is grasped (preferably along with lobe 30*a*, 80*a*, or 90*a*, as appropriate), and the remainder of wax guard 30, 80, or 90, peeled from release liner 60. Center lobe 30*c*, 80*c*, or 90*c* is then positioned over and circumferentially adhered to the sound outlet end of hearing aid 50 and exposed lobe 30*p*, 80*p*, or 90*p* then adhered to the posterior side of hearing aid 50. Wing 70*a* of folded release liner 70 is then removed from lobe 30*a*, 80*a*, or 90*a* while the latter is being adhered to the anterior side of hearing aid 50**.

For convenience, the linered wax guard assembly shown in FIG. 7 can be distributed in a transparent plastic envelope 92, which will ensure that wax guards 30, 80, and 90 do not become prematurely detached from either liner 60 or folded liner 70. It is contemplated that a kit containing a plurality of wax guards having a variety of thicknesses of reticulated open cell foam membrane 31, 81, 91 (e.g., 1/32, 1/16, and ⅛ inch, corresponding respectively to about 0.8, 1.6, and 3.2 mm) will prove useful to hearing aid dispensers, who can then provide the appropriate wax guard for an individual hearing aid wearer. Alternatively, as shown in FIG. 7, this kit could consist of wax guards in which anterior attaching lobes **30*a*, 80*a*, 90*a*** are of different dimensions As still another alternative, single adhesive-coated lobes of different dimensions could be incorporated in a kit; although these lobes would not function as wax guards, they could still be used to determine the appropriate degree of sealing to reduce or eliminate feedback caused by canal shape change resulting from jaw motion. Once the appropriate size has been determined, the adhesive-coated lobe could be used until it is soiled, after which it would be replaced with a fresh lobe. It is further contemplated that, when using the feedback suppressing aspect of the invention, shape-retaining retarded recovery materials such as plasticized polyvinyl chloride (cf. U.S. Pat. No. RE. 29,487) or polyurethane (cf. U.S. Pat. No. 4,880,076) would be more efficient than the open cell reticulated foam used for wax entrapment and hence could be used in thinner sections.

Those skilled in the art will readily appreciate that the foregoing description is not intended to be exhaustive, and numerous variations of the invention can be made without departing from the spirit of what has been taught. Thus, for example, although wax guards having two attaching lobes are currently preferred, it would be feasible to have four, the additional lobes attaching to the superior and inferior surfaces of the hearing aid. The greater the number of lobes, however, the greater the difficulty in attaching the wax guard. It should be possible to prepare a wax guard having a single attaching lobe (preferably the anterior lobe), the adhesive border on the center lobe holding it in place over the sound outlet port. It may also be possible to prepare a product that has a single continuous lobe, resulting in a construction resembling that of a condom.

Similarly, the utility of the invention is not limited to hearing aids, but is readily adaptable to any type of sound transmitting device that intrudes into the ear canal.

At the present time, the preferred dimensions of wax guard 30 are about 18.5 mm from the distal end of lobe **30*a* to the distal end of lobe 30*p*, lobe 30*a* being about 7.4 mm long and 6.6 mm wide. Lobe 30*p* is about 4.8 mm long and 5.6 mm wide. Central lobe 30*c* is about 8.9 mm wide. Although these exact dimensions and shapes are not critical, such products are suitable for mounting on all known "in the ear" hearing aids. Wax guards having the shape of wax guard 10 are useful on most hearing aids, although they may be somewhat difficult to install smoothly on hearing aids that fit into concha 42 and do not penetrate as far into canal 43 as hearing aids that fit almost entirely into canal 43**.

Although numerous pressure-sensitive adhesives may be used to mount wax guard 10 or 30 on hearing aid 50, acrylate types are presently preferred; acrylate adhesives (e.g., a 95:5 isooctyl acrylate:acrylic acid copolymer) adhere well to the acrylate polymers used to make most hearing aids. Acrylate adhesives also tend not to irritate skin with which they may come in contact.

What is claimed is as follows:

1. For use in connection with a sound transmitting device of the type in which a housing contains a sound transmitting tube having a sound outlet port confronting the ear drum when said device is fitted within a user's ear canal, a disposable wax guard for mounting over the sound outlet port to prevent cerumen from fouling said outlet port, said wax guard being readily installed and replaced by a user, comprising a thin, flexible membrane that permits a user to position said guard over said outlet port, one side of said membrane being provided with a normally tacky and pressure-sensitive adhesive layer except in that portion adapted to overlie said outlet port, the portion of said guard overlying said outlet port being porous to sound and capable of wax entrapment.

2. The wax guard of claim 1 wherein the means for temporarily adhering said wax guard in position is a normally tacky and pressure-sensitive adhesive tape.

3. For use in connection with an "in the ear" hearing aid of the type in which a housing having an anterior side and a posterior side and containing a microphone, an amplifier, and a speaker is fitted within the user's ear canal so that a portion of said housing confronts the user's ear drum, said ear canal having an anterior wall and a posterior wall, the anterior side of the hearing aid housing confronting said anterior wall and the posterior side of said housing confronting said posterior wall, with a sound-transmitting tube extending from adjacent the speaker to a sound outlet port at the portion of the housing nearest to the ear drum, a disposable wax guard for mounting over the sound outlet port to prevent cerumen from fouling said outlet port, comprising a thin, flexible carrier membrane adapted to be positioned by a user so as to overlie said outlet port, one side of said membrane being provided with a normally tacky and pressure-sensitive adhesive layer except in that portion adapted to overlie the sound outlet port the portion of said guard overlying said outlet port being porous to sound and capable of wax entrapment.

4. The wax guard of claim 3 wherein the membrane is compressible, resilient open cell foam.

5. The wax guard of claim 4 wherein the membrane is configured to have a plurality of lobes that can be removably adhered to the hearing aid housing In the area adjacent to the sound outlet port.

6. The wax guard of claim 5 wherein there are only two lobes, and they are adapted to adhere respectively to the anterior and posterior sides of the hearing aid housing.

7. The wax guard of claim 6 wherein the two lobes are of unequal size.

8. The wax guard of claim 7 wherein the lobes are removably adhered to the face of a release liner.

9. The product of claim 8 wherein one lobe of the wax guard is removably adhered to the face of a folded release liner and the remainder of the wax guard is adhered to the face of a separate release liner.

10. The product of claim 9 wherein the larger lobe of the wax guard is adhered to the folded liner.

11. A kit containing a plurality of individual wax guards as called for in claim 10, the thickness and/or size of the open cell foam membrane being different on the individual guards.

12. The wax guard of claim 3 wherein the normally tacky and pressure-sensitive adhesive layer is in the form of a double-coated tape.

13. The wax guard of claim 3 wherein the sound-porous portion of the membrane is a hole having a slightly larger diameter than that of the outlet port, a mat of nonwoven fibers overlying said hole and being adhered to the portions of said membrane circumjacent to said hole.

14. The wax guard of claim 13 wherein the nonwoven mat is oleophilic.

15. The wax guard of claim 13 wherein the nonwoven mat consists essentially of blown microfibers.

16. The wax guard of claim 15 wherein the blown microfibers are polypropylene.

17. The wax guard of claim 15 wherein the membrane is provided with a normally tacky and pressure-sensitive adhesive circumjacent to said hole so that said guard can be removably attached to the hearing aid housing in the area adjacent to the sound outlet port.

18. The wax guard of claim 17 wherein the membrane is configured to have a plurality of lobes that can be removably adhered to the hearing aid housing In the area adjacent to the sound outlet port.

19. The wax guard of claim 18 wherein there are only two lobes and they are adapted to adhere respectively to the anterior and posterior sides of the hearing aid.

20. An "in the ear" hearing aid having a sound outlet port, the wax guard of claim 3 being mounted over said outlet port and adhered to the housing of the hearing aid.

* * * * *